(12) United States Patent
Wycoff

(10) Patent No.: US 8,389,025 B2
(45) Date of Patent: Mar. 5, 2013

(54) COMPOSITIONS TO ALLEVIATE HERPES VIRUS SYMPTOMS

(75) Inventor: Jeffrey Wycoff, Boulder, CO (US)

(73) Assignee: Paradigm, Inc., Longmont, CO (US)

( * ) Notice: Subject to any disclaimer, the term of this patent is extended or adjusted under 35 U.S.C. 154(b) by 4 days.

(21) Appl. No.: 12/658,993

(22) Filed: Feb. 17, 2010

(65) Prior Publication Data

US 2010/0151052 A1 Jun. 17, 2010

Related U.S. Application Data

(63) Continuation of application No. 12/002,042, filed on Dec. 14, 2007, now abandoned.

(60) Provisional application No. 60/875,018, filed on Dec. 15, 2006.

(51) Int. Cl.
*A61K 36/00* (2006.01)
*A61K 33/22* (2006.01)
*A61K 33/14* (2006.01)

(52) U.S. Cl. .......... 424/725; 424/658; 424/680

(58) Field of Classification Search .......... None
See application file for complete search history.

(56) References Cited

U.S. PATENT DOCUMENTS

| 6,248,307 | B1 | 6/2001 | Borneman et al. |
| 2003/0003482 | A1 | 1/2003 | Halle et al. |
| 2005/0129789 | A1 | 6/2005 | Shirota |
| 2005/0255166 | A1 | 11/2005 | Moloney |

FOREIGN PATENT DOCUMENTS

| CN | 1342491 | 4/2002 |
| RU | 2001402 | 10/1993 |

OTHER PUBLICATIONS

Ernst, is homeopathy a clinically valuable approach? Trends in pharmacological sciences 26 911): 657-548, 2005.*
Kleijnen et al, Clinical trails of homoeopathy, BMJ 302: 316-323, 1991.*
Weissmann, Homeopathy: Holmes, Hogwarts, and the price of Wales, The FASEB Journal 20: 1755-1757, 2006.*
Ernst et al, Efficacy of homeopathic Arnica, Arch Surg 133: 1187-1190, 1998.*
Ernst, A systematic review of systematic reviews of homeopathy, Br J Clin Pharmacol 54: 577-582, 2002.*
U.S. Appl. No. 12/002,042, filed Dec. 14, 2007.
U.S. Appl. No. 60/875,018, filed Dec. 15, 2006.
McKeon. Herbal Management of Diabetic Leg Ulcers. Australian Journal of Medical Herbalism, 6(4): 99, 1994.

* cited by examiner

*Primary Examiner* — Qiuwen Mi
(74) *Attorney, Agent, or Firm* — Craig R. Miles; CR Miles, P.C.

(57) ABSTRACT

Compositions and methods of preparing and using such compositions to treat the symptoms of herpes virus.

4 Claims, 6 Drawing Sheets

| MATERIAL | POTENCY DESIGNATION |
| --- | --- |
| Rhus toxicondendron | between about 6x and about 200c HPUS |
| Ranunculus bulbosus | between about 3x and about 200c HPUS |
| Phytolacca decandra | between about 3x and about 200c HPUS |
| Crab Apple | between about 3x and about 200c HPUS |
| Natrum muriaticum | between about 3x and about 200c HPUS |
| Borax | between about 1x and about 200c HPUS |

FIGURE 1

| MATERIAL | POTENCY DESIGNATION | |
|---|---|---|
| Rhus toxicondendron | 30x | HPUS |
| Ranunculus bulbosus | 12x | HPUS |
| Phytolacca decandra | 3x | HPUS |
| Crab Apple | 5x | HPUS |
| Natrum muriaticum | 30x | HPUS |
| Borax | 1x | HPUS |

FIGURE 2

| MATERIAL | POTENCY DESIGNATION | |
|---|---|---|
| Rhus toxicondendron | 30x | HPUS |
| Ranunculus bulbosus | 12x | HPUS |
| Phytolacca decandra | 3x | HPUS |
| Crab Apple | 1x | HPUS |
| Succinic acid | 15 milligrams (mg) | |

FIGURE 3

| MATERIAL | POTENCY DESIGNATION | |
|---|---|---|
| Rhus toxicondendron | 30x | HPUS |
| Ranunculus bulbosus | 12x | HPUS |
| Phytolaccca decandra | 3x | HPUS |
| Crab Apple | 1x | HPUS |
| Natrum muriaticum | 30x | HPUS |
| Borax | 1x | HPUS |

FIGURE 4

| MATERIAL | POTENCY DESIGNATION | |
|---|---|---|
| Mezereum | 12x | HPUS |
| Phytolacca decandra | 12x | HPUS |
| Ranunculus bulbosus | 12x | HPUS |
| Rhus toxicodendron | 12x | HPUS |
| Sepia | 30x | HPUS |
| Natrum Muriaticum | 12x | HPUS |
| Clematix | 12x | HPUS |
| Influenzinum | 18x | HPUS |

FIGURE 5

| MATERIAL | POTENCY DESIGNATION | |
|---|---|---|
| Mezereum | 12x | HPUS |
| Phytolacca decandra | 12x | HPUS |
| Ranunculus bulbosus | 12x | HPUS |
| Rhus toxicodendron | 12x | HPUS |
| Natrum Muriaticum | 12x | HPUS |
| Clematix | 12x | HPUS |
| Influenzinum | 18x | HPUS |

FIGURE 6

COMPOSITIONS TO ALLEVIATE HERPES VIRUS SYMPTOMS

This United States Patent Application is a continuation of U.S. patent application Ser. No. 12/002,042 (now abandoned), filed Dec. 14, 2007, and claims the benefit of U.S. Provisional Patent Application No. 60/875,018 filed Dec. 15, 2006, each hereby incorporated by reference herein.

I. BACKGROUND

Compositions and methods of preparing and using such compositions to treat the symptoms of herpes virus.

The herpes simplex virus (HSV) is a virus that manifests itself in two common viral infections, each marked by painful, watery blisters in the skin or mucous membranes (such as the mouth or lips) or on the genitals. The disease is contagious, particularly during an outbreak, and is incurable with present technology. An infection on the lips is commonly known as a "cold sore" or "fever blister". These are sometimes confused with canker sores or aphthous ulcers, which have a similar appearance; these appear inside the mouth and are not caused by the herpes simplex virus. When asymptomatic, HSV lies dormant in the bodies of the nerve cells, replicating within the axons towards the skin during an outbreak. When the outbreak has passed, the virus 'dies back' along the nerve until it is only present in the nerve body. The dormancy of the virus within the nerve bodies contributes to the difficulty of treatment.

There is currently no cure or vaccine for HSV. Treatment in the form of antiviral medications such as Acyclovir (trade name Zovirax), Famciclovir, pancyclovir, valacyclovir, or the like, which reduce the duration of symptoms and accelerates healing are available. Treatment typically begins at the first symptoms of an outbreak.

Another option is the use of daily suppressive therapy, in which antivirals are taken every day over the course of years. Suppressive therapy may reduce frequency of symptoms and recurrence of outbreaks. In addition, suppressive therapy reduces subclinical shedding, lowering the risk of transmission through sexual contact or kissing.

A substantial problem with taking antiviral medications can be side effects such as confusion, hallucinations, increased thirst, redness, blistering, peeling or loosening of the skin, including inside the mouth, reduced amount of urine passed, seizures, skin rash or hives, stomach pain, tremor, unusual weakness or tiredness, diarrhea, dizziness, headache, increased sensitivity to the sun, loss of appetite, nausea, or vomiting.

Due to the various adverse effects associated with antiviral drug therapy, certain herbal remedies have been utilized to alleviate herpes virus symptoms such as pau d'arco, echinacea, burdock root, nettle, chamomile, St. John's wort, skullcap, passionflower, goldenseal, comfrey leaf, calendula, or chapparal leaves or combinations thereof. Homeopathic remedies have also been utilized to alleviate herpes virus symptoms such as *Natrum Muriaticum, Rhus toxicodendron, Mercurius, Sepia*, or combinations thereof.

Homeopathic products useful in treating herpes virus symptoms are described in the Homeopathic Pharmacopeia of the United States (HPUS). There are benefits to utilizing herbal and homeopathic remedies because they appear to reduce certain herpes virus symptoms and because the compliance rate can be high while the rate of side effects can be low.

Despite advances in the art of herbal and homeopathic remedies, there remains a need for additional compositions, formulations, mixtures, potency dilution admixtures, or the like and methods of preparing and using such compositions, formulations, potency dilution admixtures, or the like to treat the symptoms of herpes virus which as compared to conventional compositions, formulations, mixtures, potency dilution admixtures provide alternative treatment with respect to the active ingredient or manner of delivery thereof or reduce to a greater degree herpes virus symptoms.

II. SUMMARY OF THE INVENTION

Accordingly, a broad object of the invention can be to provide compositions, formulations, and potency dilution admixtures for the treatment of herpes virus symptoms.

Another broad object of the invention can be to provide improved methods for preparing formulations, particularly with respect to oral and topical dosage forms, useful in treating herpes virus symptoms.

Another broad object of the present invention can be to provide methods of treating herpes virus symptoms such as treatment preventing or providing a reduction in the frequency or severity of at least one such symptom, or both the frequency or severity of at least one such symptom, or otherwise mitigating such symptoms.

Another broad object of the invention can be to provide methods of preparing an oral dosage form for the treatment of herpes virus symptoms. Such dosage forms may be prepared by admixing or combining the requisite amounts of homeopathic or herbal components, or both, together with any pharmaceutical excipients, and dividing the mixture into unit doses containing an appropriate amount of the admixture or combination to treat herpes virus symptoms when administered to a person whether in solid unit dosage or topical forms such as creams or liquids.

Another broad object of the invention can be to provide a method of treating herpes virus symptoms by administering a unit dose of the homeopathic components herein described orally to a person as a treatment for herpes virus symptoms.

Another broad object of the invention can be to provide a method of treating herpes virus symptoms by administering a unit dose of the homeopathic components herein described topically to a person as a treatment for herpes virus symptoms.

Naturally, further objects of the invention are disclosed throughout other areas of the specification, drawings, photographs, and claims.

III. A BRIEF DESCRIPTION OF THE DRAWINGS

FIGS. 1-6 each provide non-limiting examples of particular embodiments of the inventive compositions encompassed by the invention.

IV. DETAILED DESCRIPTION OF THE PREFERRED EMBODIMENTS

Compositions and methods of preparing and using such compositions to treat the symptoms of herpes virus.

The process of homeopathic drug preparation is based on the concept of potentization or potentiation. Homeopathy relies on the administration of successively more diluted formulations of key homeopathic components to affect a desired response. The manufacturing process underlying this philosophy, therefore, requires the preparation of dilutions that represent very small fractions of the original base product's composition. Products available commercially or prepared by homeopathic physicians and pharmacists may be combined with alcohol, distilled water, or lactose as their dilution matrix. Mother tincture (also referred to as "Ø") typically refers to a crude homeopathic compound that is triturated in alcohol.

Potency designations refer to the dilution of the mother mix. One part drug mixed with 9 parts dilution matrix is designated a 1× potency. A potency designation of 10× (or 1 c) is composed of 1 part mother tincture diluted in 99 parts of a selected diluent. A potency designation 1 m is 1 part mother tincture mixed in 999 parts of selected dilution. A potency of 2× is 1 part 1× potency and 9 parts of dilution. Low potency examples are 1×, 6×, 6 c. Examples of medium potency include 30× and 30 c. High potency examples are 200c, 1 m, 20 m.

"HPUS" as referred to herein means a material prepared in accordance to the specifications of the Homeopathic Pharmacopoeia of the United States, hereby incorporated by reference herein.

The term "composition" as used herein refers to any single material or combination, mixture, or admixture of materials, or admixture of dilution potencies, or mixture of diluted materials (whether diluted as mixtures of active substances with excipients as solids or diluted as mixtures of active substances with excipients as liquids), or the like, an amount of which can provide a dose, or an amount of which can be divided into a plurality of doses, or can be divided into amounts a plurality of which can be combined to provide a dose (such as two or more capsules, tablets, drops, or measures of a powder, or the like). A "dose" upon administration to a patient affects herpes virus symptoms as above-described. The term "dosage form" as used herein refers to a dose established in any manner capable of delivery to a patient and without limitation includes solid dosage forms such as an amount powder, an amount of effervescent powder, an amount of the composition pressed or compacted to provide a solid typically configured to be swallowed such as a tablet, or a plurality of tablets, or a number of tablets which individually or in combination provide a dose, a caplet, a capsule which contains an amount of the composition, and further includes liquid dosage forms such as an amount of liquid, a drop of liquid, a plurality of drops of liquid, or a number of drops of liquid which individually or in combination allow delivery of a dose. The term oral dosage form whether a liquid oral dosage form or a solid oral dosage form provides delivery of a dose by introduction of the dosage form(s) whether liquid or solid into the mouth. The term "tablet" as used herein refers to an amount of the composition pressed or compacted or otherwise established in a solid form (including without limitation the active substances applied as liquids to pressed or compacted amounts of excipients in solid form) configured to be taken orally.

Generally, a dosage form can include a composition which provides in sufficient amount an admixture of *Rhus toxicondendron*, *Ranunculus bulbosus*, *Phytolacca decandra*, and *Malus pumila* for treatment of herpes virus symptoms in a patient. Other dosage forms can further include at least one component such as an amount of *Natrum muriacticum* or an amount of Borax, or as to other dosage forms both *Natrum muriacticum* and Borax can be included.

Now referring primarily to FIG. 1 and Table 1, certain homoeopathic embodiments of the composition can provide an amount of *Rhus toxicondendron* of between about 6×HPUS and about 200c HPUS, an amount of *Ranunculus bulbosus* of between about 3×HPUS and about 200c HPUS, an amount of *Phytolacca decandra* of between about 3×HPUS and about 200c HPUS, an amount of *Malus pumila* of between 1× and about 200c (or an equivalent molar amount of each component). The dosage form can further include an amount of *Natrum muriacticum* of between about 3×HPUS and about 200c HPUS or can include an amount of Borax of between about 6×HPUS and about 200c HPUS, or can include both an amount of *Natrum muriacticum* of between about 3×HPUS and about 200c HPUS and an amount of Borax of between about 6×HPUS and about 200c HPUS (or the equivalent molar amount of each).

As to those embodiments of the invention which provide an oral solid dosage form, the oral solid dosage form retains the original HPUS strength of dilution as above described or as set out in FIGS. 1-6 or Tables 1-6 below depending on the embodiment. Particular embodiments of an oral solid dosage form can be a tablet dosage form which provides an admixture of an amount *Rhus toxicondendron*, an amount *Ranunculus bulbosus*, an amount *Phytolacca decandra*, and an amount *Malus pumila*. An amount of *Natrum muriaticum* or an amount of Borax (or an amount of both) can be admixed. Now referring primarily to FIG. 2 and Table 2, as but one non-limiting example, a preferred oral dosage form can comprise a tablet which provides *Rhus toxicondendron* (Poison Ivy) 30×HPUS, *Ranunculus bulbosus* (Buttercup) 12×, *Phytolacca decandra* (Pokeroot) 3×, *Malus pumila* (Crab Apple) 5×, *Natrum muriaticum* (Sodium Chloride) 30×, and Borax (Sodium Borate) 1× and further including excipients admixed providing an amount of Magnesium Stearate, Microcrystalline Cellulose, and Sucrose which can be divided and compressed to form a tablet of a configuration and weight suitable for oral administration.

A preferred non-limiting tablet dosage form including the active ingredients and inactive ingredients as above-described can provide a circular geometry with a diameter of between about 9.0 millimeters to about 10.0 millimeters and a thickness of between about 4.00 millimeters to about 5.00 millimeters providing a weight of between about 0.290 and about 0.310 grams. The tablet can have a hardness of between about 2.5 Kp and about 5.0 Kp with a friability of less than about 1 percent which disintegrates in less than 30 minutes. This particular embodiment of an oral solid dosage form is not intended to be limiting with respect to the numerous and varied oral solid dosage forms which can provide a dose for the treatment of symptoms of herpes virus, but rather it is intended to provide a person of ordinary skill in the homeopathic field a description sufficient to make and use the numerous and varied embodiment of the invention encompassed by this description.

A non-limiting example of a dose for the treatment of cold sore or oral herpes virus symptoms and a non-limiting example of a method of treating herpes virus symptoms (including treatment with the particular oral dosage form of a tablet described above) can include chewing three tablets at the first sign of herpes virus symptoms such as burning or itching, and then chewing three tablets three times daily until symptoms disappear. A non-limiting example of a dose for the treatment of genital herpes symptoms and a non-limiting example of a method of treating genital herpes symptoms (including treatment with the particular oral dosage form of a tablet described above) can include chewing between 3 and 5 tablets 3 times daily for prevention of outbreaks and at the first sign of herpes virus symptoms such as burning or itching, and then chewing 3 tablets 3 times daily until symptoms disappear.

A method of preparing a dosage form of a homeopathic composition can include the steps of admixing a sufficient amount of *Rhus toxicondendron*, *Ranunculus bulbosus*, *Phytolacca decandra*; and *Malus pumila* to establish a mixture and dividing said mixture to provide a plurality of a dosage form. The method can further comprise the step of admixing a sufficient amount of at least one of *Natrum muriacticum* or Borax (or both). The method can further include the step of admixing an amount of excipients such as Magnesium Stearate, Microcrystalline Cellulose, and sucrose in various combinations and permutations.

Now referring primarily to Table 2 and FIG. 2, one non-limiting method of preparing a dosage form of a homeopathic composition can include the steps of admixing an amount of a mother trituration *Rhus toxicondendron* 27×HPUS, *Ranunculus bulbosus* 9×HPUS, *Malus pumila* 2×, and *Natrum muriaticum* 27× of about 0.67 percent by weight (weight of a component divided by the total weight of the final prepared mixture) with an amount of microcrystalline cellulose (such as Emcocel 90M) about 6.0 percent by weight in a blender (such as a V-blender or tumble blender) for about 30 minutes. To this mixture, admix an amount of compressible sucrose (such as Easy-Fond) about 76.5 percent by weight, an amount of microcrystalline cellulose about 11.9% by weight, an amount of Borax about 1.67% by weight, and an amount of Phytolacca Decandra 2× (yield from first tituration of Phytolacca Decandra 1× (about 475 grams) admixed with Lactose, Anyydrous, USP (4,750 grams)) about 1.67 percent by weight in a tumble blender for about 55 minutes. To this mixture, admix magnesium stearate about 2.0% by weight in a tumble blender for about 5 minutes. Screen the finished mixture through a 20 mesh screen and transfer to a vessel for storage. Subsequently, compress into a tablet dosage form of the above-described configuration and dose or the other chewable configuration or dose depending on the formulation.

As to those embodiments of the invention which provide a topical dosage form (such as an amount of a liquid or an amount of a cream) the original HPUS strength of dilution as above described or as set out in FIGS. 1-6 or Tables 1-6 below can be maintained. As to particular embodiments of a topical dosage form, a cream or a liquid can provide an admixture of an amount *Rhus toxicondendron*, an amount *Ranunculus bulbosus*, an amount *Phytolacca decandra*, and an amount *Malus pumila* to which an amount of *Natrum muriaticum* or an amount of Borax (or an amount of both) can be admixed. Now referring primarily to FIG. 4 and Table 4 as but one non-limiting example, a preferred topical dosage form can comprise a cream or a liquid which provides *Rhus toxicondendron* (Poison Ivy) 30×HPUS, *Ranunculus bulbosus* (Buttercup) 12×, *Phytolacca decandra* (Pokeroot) 3×, *Malus pumila* (Crab Apple) 1×, *Natrum muriaticum* (Sodium Chloride) 30×, and Borax (Sodium Borate) 1× admixed into an amount of lactose, magnesium stearate, microcrystalline cellulose to form a cream for topical administration or an amount of distilled water to provide a liquid for topical administration.

Now referring to FIG. 1 and Table 1, a first exemplary embodiment of the inventive compositions to alleviate or reduce symptoms of herpes virus, can include in an oral dosage form (such as a tablet or capsule) or a topical dosage form the following formulation:

TABLE 1

| MATERIAL | POTENCY DESIGNATION |
| --- | --- |
| *Rhus toxicondendron* | between about 6x and about 200 c HPUS |
| *Ranunculus bulbosus* | between about 3x and about 200 c HPUS |
| *Phytolacca decandra* | between about 3x and about 200 c HPUS |
| Crab Apple | between about 3x and about 200 c HPUS |
| Natrum muriaticum | between about 3x and about 200 c HPUS |
| Borax | between about 1x and about 200 c HPUS |

Now referring to FIG. 2 and Table 2, a second exemplary embodiment of the inventive compositions to alleviate or reduce symptoms of herpes virus, can include in an oral dosage form (such as a tablet or capsule) the following formulation:

TABLE 2

| MATERIAL | POTENCY DESIGNATION |
| --- | --- |
| *Rhus toxicondendron* | 30x HPUS |
| *Ranunculus bulbosus* | 12x HPUS |
| *Phytolacca decandra* | 3x HPUS |
| Crab Apple | 5x HPUS |
| Natrum muriaticum | 30x HPUS |
| Borax | 1x HPUS |

Now referring to FIG. 3 and Table 3, a third exemplary embodiment of the inventive compositions to alleviate or reduce symptoms of herpes virus, can include in an oral dosage form (such as a tablet or capsule) the following formulation:

TABLE 3

| MATERIAL | POTENCY DESIGNATION |
| --- | --- |
| *Rhus toxicondendron* | 30x HPUS |
| *Ranunculus bulbosus* | 12x HPUS |
| *Phytolacca decandra* | 3x HPUS |
| Crab Apple | 1x HPUS |
| Succinic acid | 15 milligrams (mg) |

Now referring to FIG. 4 and Table 4, a fourth exemplary embodiment of the inventive compositions to alleviate or reduce symptoms of herpes virus, can include in a topical dosage form such as an ointment, cream, or liquid the following formulation:

TABLE 4

| MATERIAL | POTENCY DESIGNATION |
| --- | --- |
| *Rhus toxicondendron* | 30x HPUS |
| *Ranunculus bulbosus* | 12x HPUS |
| *Phytolaccca decandra* | 3x HPUS |
| Crab Apple | 1x HPUS |
| Natrum muriaticum | 30x HPUS |
| Borax | 1x HPUS |

Now referring to FIG. 5 and Table 5, a fifth exemplary embodiment of the inventive compositions to alleviate or reduce symptoms of herpes virus, can include in a topical dosage form such as an ointment or a cream the following formulation:

TABLE 5

| MATERIAL | POTENCY DESIGNATION |
| --- | --- |
| *Mezereum* | 12x HPUS |
| *Phytolacca decandra* | 12x HPUS |
| *Ranunculus bulbosus* | 12x HPUS |
| *Rhus toxicodendron* | 12x HPUS |
| *Sepia* | 30x HPUS |
| Natrum Muriaticum | 12x HPUS |
| Clematix | 12x HPUS |
| Influenzinum | 18x HPUS |

Now referring to FIG. 6 and Table 6, a fifth exemplary embodiment of the inventive compositions to alleviate or reduce symptoms of herpes virus, can include in a topical dosage form such as an ointment or a cream the following formulation:

TABLE 6

| MATERIAL | POTENCY DESIGNATION |
|---|---|
| *Mezereum* | 12x HPUS |
| *Phytolacca decandra* | 12x HPUS |
| *Ranunculus bulbosus* | 12x HPUS |
| *Rhus toxicodendron* | 12x HPUS |
| Natrum Muriaticum | 12x HPUS |
| Clematix | 12x HPUS |
| Influenzinum | 18x HPUS |

Depending on the dosage form one or more of the following excipients can be admixed to the active ingredients to produce a dosage form for a particular route of administration such as a tablet, cream, gel, ointment, or liquid.
EXCIPIENT.
Lactose
Microcyrstalline cellulose
Magnesium Stearate
Calcium phosphate
PEG8000
Silicon dioxide
Glycerol monostearate
Water

*Rhus toxicondendron* is a pacific poison ivy the leaves and stalks of the plant can be pulverized and mixed with alcohol. The mixture is strained and diluted. The strained mixture can be utilized in the inventive composition dosage form prepared in accordance with the HPUS of between about 3x and 200c potency.

*Ranunculus bulbosus* is commonly referred to the bulbous buttercup the leaves and stalks of the plant or the whole plant can be pulverized and mixed with alcohol. The mixture is strained and diluted. The strained mixture can be utilized in the inventive composition dosage form prepared in accordance with the HPUS of between about 3x and 200c potency.

*Phytolacca decandra* is commonly referred to as poke. The root of the plant can be pulverized and mixed with alcohol. The mixture is strained and diluted. The strained mixture can be utilized in the inventive composition dosage form prepared in accordance with the HPUS of between about 3x and 200c potency.

Succinic acid is a solid that forms colorless, odorless crystals. It has a melting point of 185° C. and a boiling point of 235° C. It is a diprotic acid. The anion, succinate, is a component of the citric acid cycle and is capable of donating electrons to the electron transfer chain and with respect to the dosage formulation of Table 3 between about 10 mg and 20 mg can by utilized per dose with a preferred embodiment including about 15 mg per dose.

*Natrum muriaticum* commonly known as sodium chloride or salt. Sodium chloride can be dissolved in hot, boiling water. The mixture is then filtered and crystallized through evaporation. The resulting substance is then dissolved in water and succussed to create the final preparation of between about 3x to about 200c.

Borax or sodium borate can be dissolved in hot, boiling water. The mixture is then filtered and crystallized through evaporation. The resulting substance is then dissolved in water and succussed to create the final preparation which can be between about 1x to about 200c.

*Daphne mezereum* is a species of *Daphne* in the flowering plant family Thymelaeaceae, native to most of Europe and western Asia, north to northern England and central Scandinavia. The bark of the plant can be pulverized and mixed with alcohol. The mixture is strained and diluted. The strained mixture can be utilized in the inventive composition dosage form prepared in accordance with the HPUS of between about 3x and 30x potency with a preferred embodiment of about 12x.

Sepia is the discharge used by the cuttlefish to disappear from a predator. Homeopaths use sepia to treat symptoms of apathy and weakness. The composition dosage form prepared in accordance with the HPUS of between about 3x and 30x potency with a preferred embodiment of about 30x.

Clematix HPUS in a potency of about 6x to about 20x with a preferred embodiment as set forth by Table 3 of about 12x.

Crabapple such as *Malus pumila* HPUS in a potency of about 1x to about 200c.

Influenzinum is a homeopathic medicine made from flu viruses. A proprietary preparation for example is produced by Dolisos pharmacy each year using the flu virus strains recommended by the World Health Organization for the year's vaccine production. The composition dosage form prepared can be about 12x and 200c potency.

Glycerol Monostearate (CAS #31566-31-1) is a lipophilic non-ionic surfactant utilized as an emulsifier available for example from ScienceLab.com or Acme-Hardesty; PEG8000 polyethylene glycol (CAS #25322-68-3) average molecular weight 8000, Calcium Phosphate (CAS #7757-93-9), Methylcellulose (CAS #9004-65-3), Silicon Dioxide (CAS #7631-86-9) available for example from Post Apple Scientific, North East Pa., can be ad mixed with the active ingredients such as in the exemplary formulation as set out in Table 3. However, it is not intended that these excipients be utilized solely with the formulation of Table 3 but can also be used with the varied and numerous formulations described within the ranges indicated whether of the admixture of Table 3 or of Tables 1 or 2.

Microcrystalline Cellulose is an excipient which as the name implies is cellulose obtained from high quality wood pulp used in the formulation of tablets and capsules. It can be used as a binding agent, due to its excellent compression properties. It also has uses as a disintegrant, in order to increase the biological availability of a medicine, and as a lubricant to aid in the tableting procedure. It is also physiologically inert, odorless and tasteless, making it suitable as a diluent in order to fill out a tablet and make a more convenient and accurate dosage form.

Magnesium Stearate, also called octadecanoic acid magnesium salt, is a white substance which is solid at room temperature used as a filling agent in the manufacture of medical tablets and capsules. In this regard, the substance is also useful because it has lubricating properties, preventing ingredients from sticking to manufacturing equipment during the compression of chemical powders into solid tablets.

Sucrose a sugar purified from sugar cane or sugar beets can be used as a base or an inactive ingredient to dilute other materials and compress to form tablets or other solid dosage forms.

Lactose a sugar obtained from milk can be used as a base or an inactive ingredient in either a hydrous or anhydrous form to dilute other materials.

It is not intended that the examples provided above be limiting with respect to the admixture of additional herbal, homeopathic, or excipient components so long as the additional components do not substantially alter the potency designation of the components as above-listed in Tables 2-6 (or the potency designation of particular embodiments of the invention in the ranges indicated in Table 1) in a dose regardless of dosage form. As such, the dosage forms of the invention may also contain pharmaceutical excipients such as fillers, binders, colorants, flavorants, or the like, whether or not specifically listed.

A dosage form by weight can include a substantial amount of pharmaceutical excipients as described above or as to other dosage forms. Regardless of the amount of excipient, the dosage forms of the present invention are prepared by admixing the components together and dividing the mixture into unit doses of desired strength, preferably such that each unit dose provides an effective amount of the components to provide relief from herpes virus symptoms when administered to a person. Due to physical limitations, a unit dose may be subtherapeutic but can be formulated to provide an effective dose when administered in multiple, i.e. two or more, unit doses or dosage forms at a time. The unit dose can be encapsulated or prepared as tablets according to conventional techniques. To prepare the finished dosage form, the herbal or homeopathic components may be admixed with pharmaceutical adjuvants and encapsulated or prepared as tablets or otherwise prepared as known in the art.

The inventive formulations, including, those formulations and potencies set out in Tables 1-6 can be utilized in tablet dosage form to reduce or alleviate symptoms of herpes virus cold sores by taking 3 tablets immediately at the first sign of burning or itching, then 3 tablets three times daily until symptoms disappear.

With respect to symptoms associated with genital herpes, the inventive formulations, including those formulations and potencies set out in Tables 1-6 can be utilized in tablet dosage form to reduce, alleviate or prevent symptoms of severe genital herpes sufferers by taking 3 to 5 tablets three times daily. If an outbreak that does not subside within 10 days, consult your doctor. For mild to moderate symptoms of genital herpes, take 3 tablets immediately at the first sign of burning or itching, and then 3 tablets three times daily until symptoms disappear. If symptoms do not subside within 10 days, consult a physician should be consulted.

The inventive formulations, including, those formulations and potencies set out in Tables 1-6 prepared as a topical ointment or liquid can be utilized by application to the affected area every 2-3 hours or as needed to reduce or alleviate symptoms of herpes virus. If symptoms do not subside within 10 days a physician should be consulted.

As can be easily understood from the foregoing, the basic concepts of the present invention may be embodied in a variety of ways. The invention involves numerous and varied compositions to alleviate herpes virus symptoms.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "homeopathic drug preparation" should be understood to encompass disclosure of the act of "preparing a homeopathic drug"—whether explicitly discussed or not—and, conversely, were there effectively disclosure of the act of "preparing a homeopathic drug", such a disclosure should be understood to encompass disclosure of a "homeopathic drug preparation" and even a "means for preparing a homeopathic drug." Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

Thus, the applicant(s) should be understood to claim at least: i) each of the compositions to treat herpes virus symptoms herein disclosed and described, ii) the related methods of treating herpes virus or herpes symptoms disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Also, the claims set forth below are intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

I claim:

1. A method of administering a composition, comprising orally administering a solid oral dosage form including an admixture of *Rhus toxicodendron, Ranunculus bulbosus, Phytolacca decandra*, and *Malus pumila*.

2. The method of claim 1, further comprising including in each said dosage form *Natrum muriacticum*.

3. The method of claim 2, further comprising including in each said dosage form Borax.

4. The method of claim 1, further comprising the step of orally administering at least two tablets.

* * * * *